(12) United States Patent
Amis

(10) Patent No.: US 6,343,531 B2
(45) Date of Patent: Feb. 5, 2002

(54) HIGH-TORQUE RESORBABLE SCREWS

(75) Inventor: James Peter Amis, San Diego, CA (US)

(73) Assignee: MacroPore, Inc.

( * ) Notice: Subject to any disclaimer, the term of this patent is extended or adjusted under 35 U.S.C. 154(b) by 0 days.

(21) Appl. No.: 09/888,786

(22) Filed: Jun. 25, 2001

Related U.S. Application Data

(63) Continuation of application No. 09/555,344, filed on May 22, 2000, now Pat. No. 6,269,716.
(60) Provisional application No. 60/066,237, filed on Nov. 20, 1997.

(51) Int. Cl.⁷ ............................................. B25B 13/06
(52) U.S. Cl. ..................... 81/121.1; 411/410; 606/73
(58) Field of Search ................ 81/121.1, 124.6, 81/125, 176.2, 186; 411/399, 402, 408, 409, 410, 500, 100, 919; 606/65, 72, 73

(56) References Cited

U.S. PATENT DOCUMENTS

| | | | | |
|---|---|---|---|---|
| 2,103,944 A | * | 12/1937 | Gullborg .................... 81/121.1 |
| 3,379,231 A | * | 4/1968 | Gallo, Sr. ...................... 81/455 |
| 3,584,667 A | * | 6/1971 | Reiland ........................ 81/460 |
| 3,596,656 A | * | 8/1971 | Kaute ........................... 606/65 |
| 3,687,501 A | * | 8/1972 | Wilson et al. ............. 403/408.1 |
| 4,142,293 A | * | 3/1979 | Tieche ......................... 433/226 |
| 4,655,661 A | * | 4/1987 | Brandt ...................... 411/387.1 |
| 4,776,329 A | * | 10/1988 | Treharne ....................... 606/65 |
| 4,973,333 A | * | 11/1990 | Treharne ....................... 606/77 |
| 5,108,399 A | * | 4/1992 | Eitenmuller et al. .......... 606/77 |
| 5,169,400 A | * | 12/1992 | Muhling et al. ............... 606/73 |
| 5,275,601 A | * | 1/1994 | Gogolewski et al. .......... 606/72 |
| 5,601,553 A | * | 2/1997 | Trebing et al. ................ 606/61 |
| 5,868,749 A | * | 2/1999 | Reed ............................ 606/76 |
| 6,166,159 A | * | 12/2000 | Ritter ....................... 526/323.1 |
| 6,269,716 B1 | * | 8/2001 | Amis ......................... 81/121.1 |

FOREIGN PATENT DOCUMENTS

FR 2745999 A * 11/1997 ............. A61F/2/08

* cited by examiner

Primary Examiner—Joseph J. Hail, III
Assistant Examiner—David B. Thomas
(74) Attorney, Agent, or Firm—Stout, Uxa, Buyan & Mullins, LLP.

(57) ABSTRACT

A high-torque fastener having a threaded shaft and a star-shaped head is disclosed. The high-torque fastener is made of a resorbable or other non-magnetic material. A mating driver snugly fits around the star-shaped head of the fastener, to thereby apply torque to the perimeter of the star-shaped head. The driver can be made disposable, and the driver and fastener packaged together in a single, disposable assembly. Additionally, the driver can be color coded to indicate the size of the fastener which is pre-attached to the driver in the packaging.

9 Claims, 5 Drawing Sheets

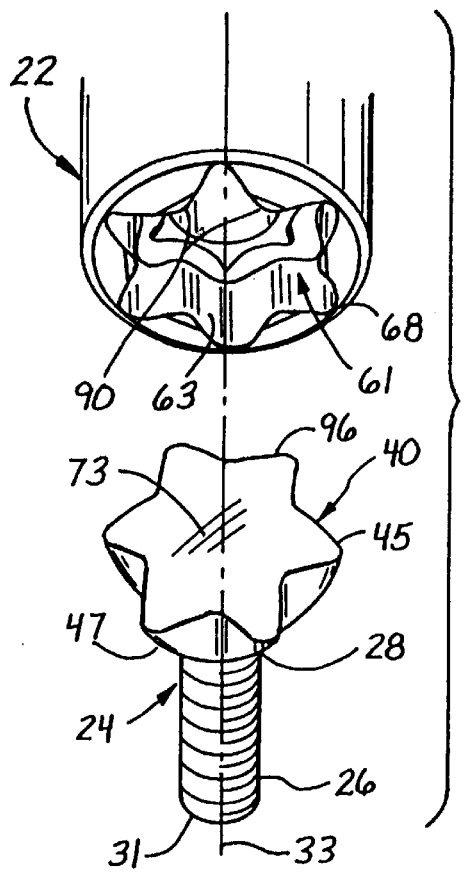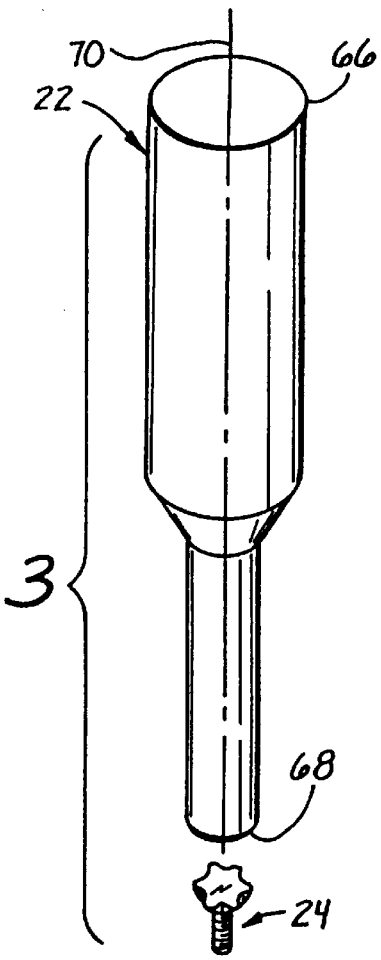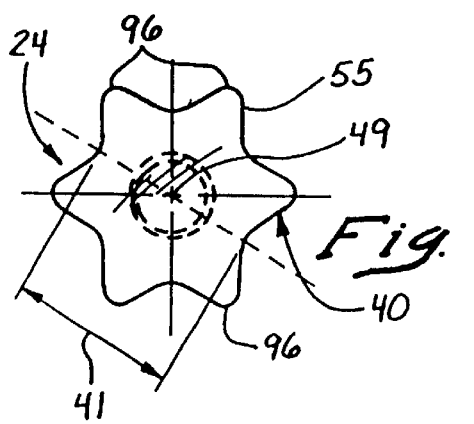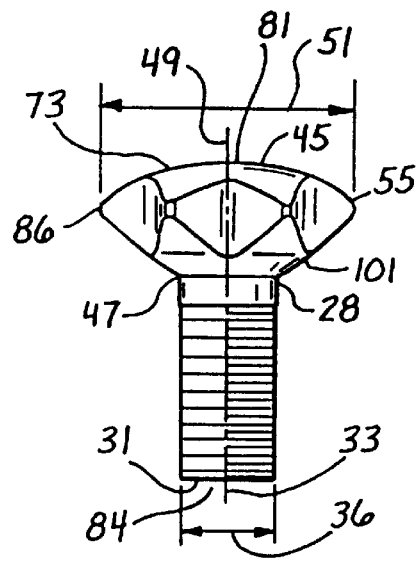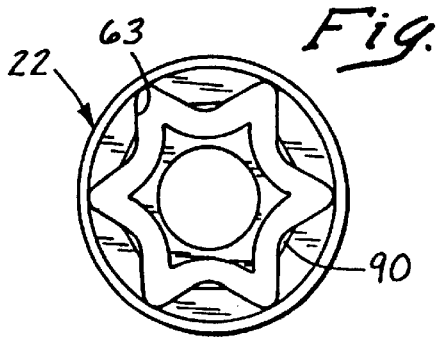

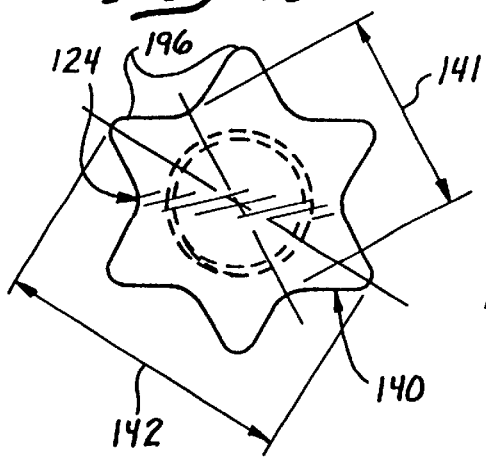
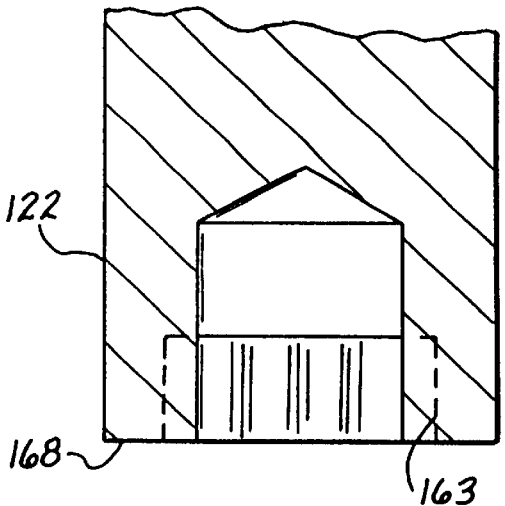
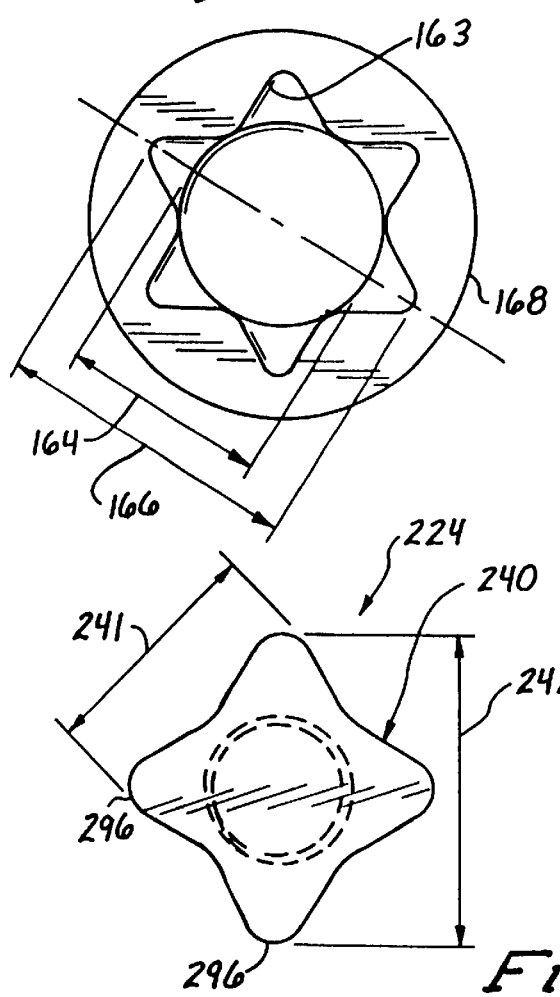
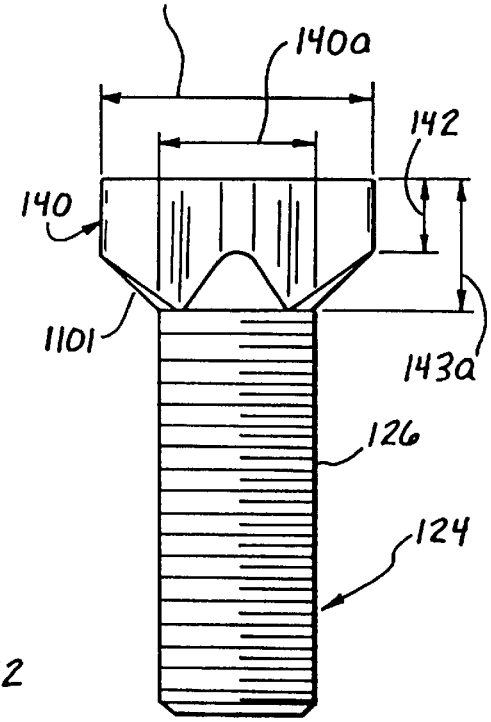

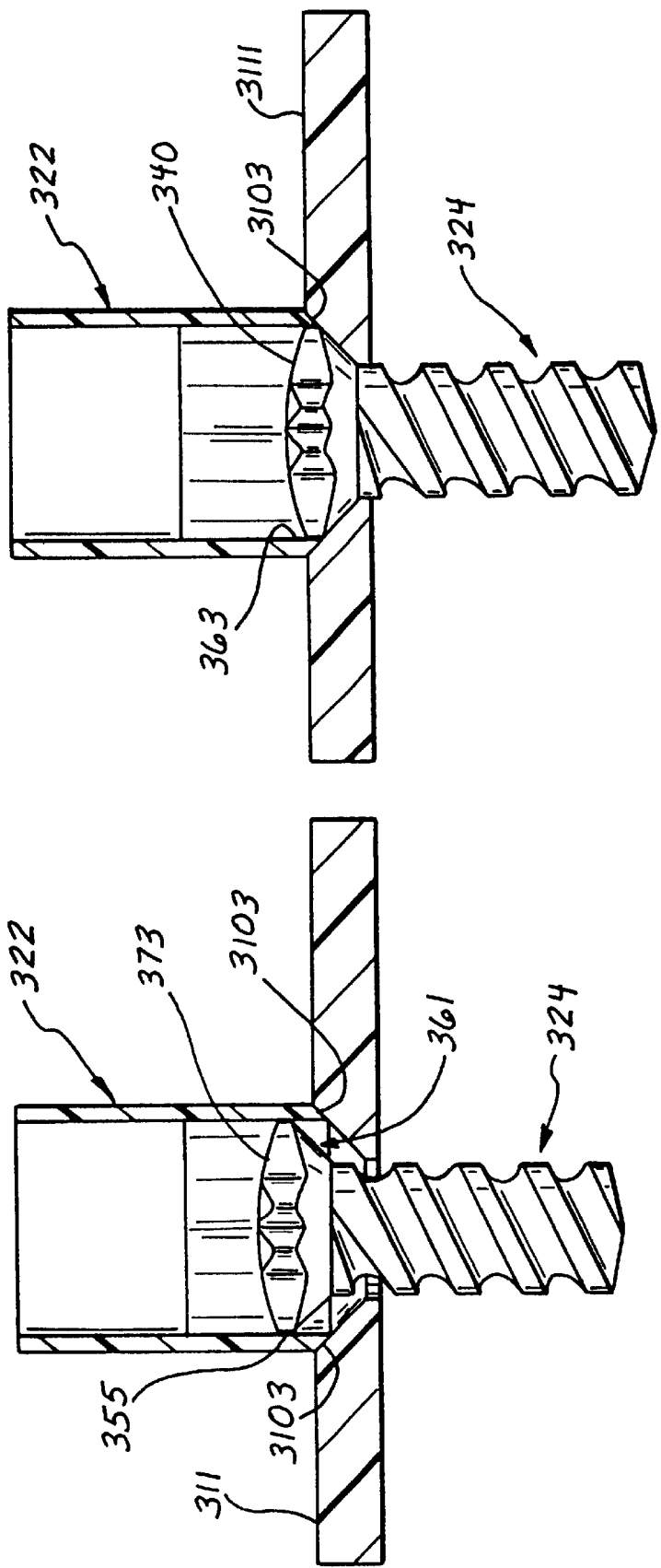

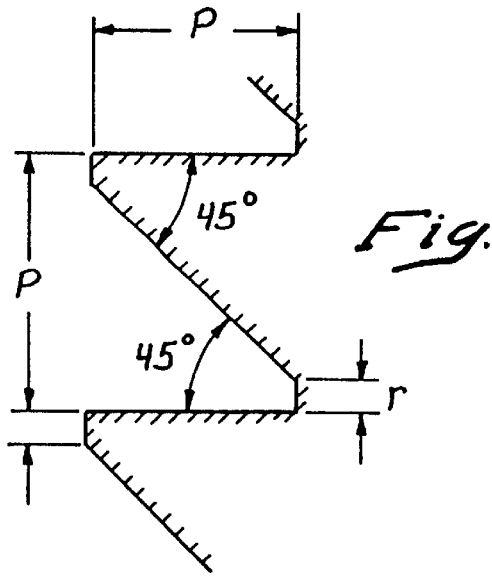
Fig. 17A
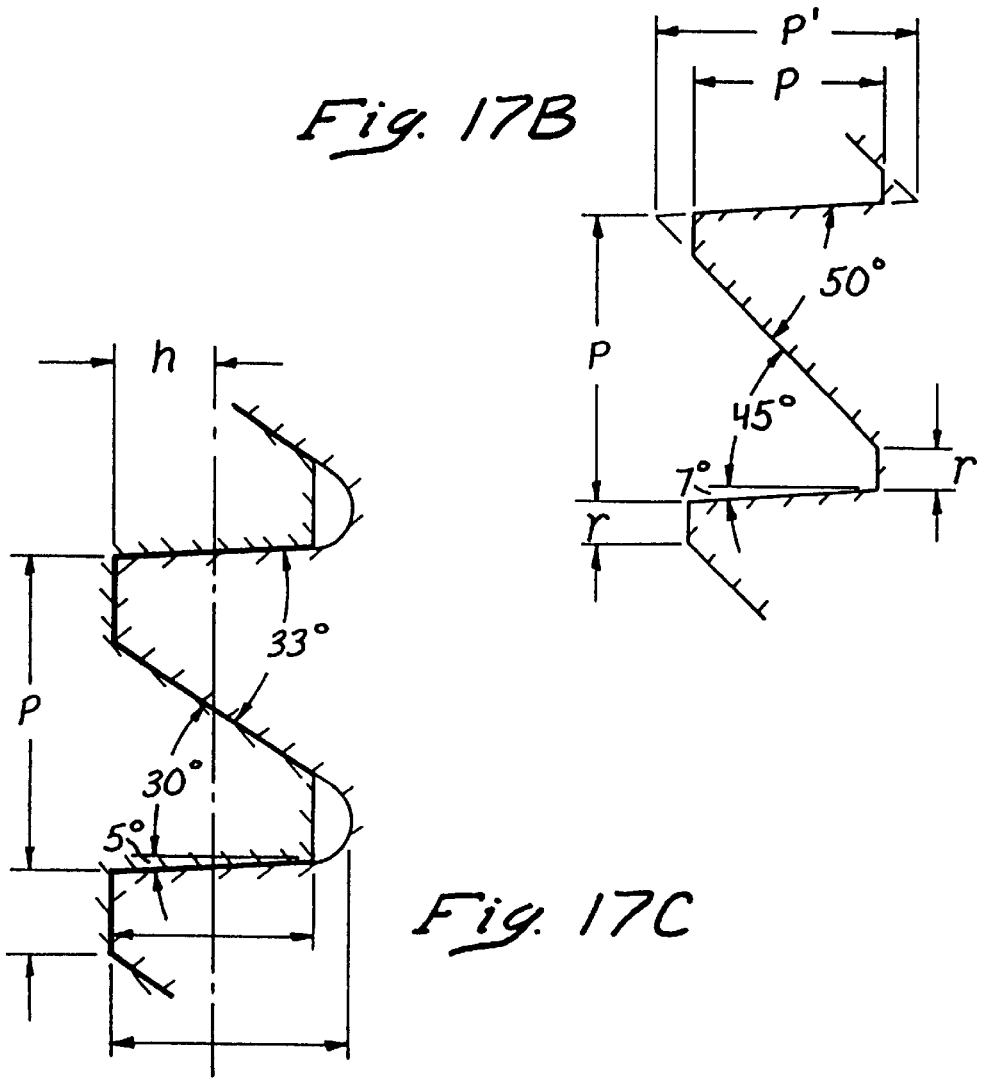
Fig. 17B
Fig. 17C

HIGH-TORQUE RESORBABLE SCREWS

This application is a continuation of U.S. application Ser. No. 09/555,344 filed May 22, 2000 issued as U.S. Pat. No. 6,269,716.

PRIORITY INFORMATION

Which application claims the benefit of U.S. Provisional Application No. 60/066,237, filed on Nov. 20, 1997 and entitled CORRUGATED DRIVE SCREW AND MATING DRIVER, the contents of which are expressly incorporated herein by reference.

RELATED APPLICATION INFORMATION

This application is related to co-pending U.S. application Ser. No. 08/699,673, issued as U.S. Pat. No. 5,919,234 filed on Aug. 19, 1996 and entitled RESORBABLE, MACRO-POROUS, NON-COLLAPSING AND FLEXIBLE MEMBRANE BARRIER FOR SKELETAL REPAIR AND REGENERATION, which is commonly assigned and the contents of which are expressly incorporated herein by reference.

BACKGROUND OF THE INVENTION

1. Field of the Invention

The present invention relates generally to fixation devices and, more particularly, to biologically compatible screws and matching drivers.

2. Description of Related Art

Since the beginning of recorded history, mankind has exhibited an insatiable appetite for constructing new devices and repairing broken ones. One meter for measuring the progress of a society through the generations has been the creativeness and craftsmanship of that societies' architects and engineers.

From ancient wooden aqueducts of the Nile, to lightweight compositional structures of the Space Shuttle, to sophisticated artificial joints of modern medicine, a common ingredient has always been the fastener. Whether the fastener is threaded, removable, or integral with the structure, an accepted engineering principle is that the strength of a product is only as great as the product's weakest link.

In the interest of promoting strength above all else, the prior art has primarily endeavored to construct metallic fasteners of varying sizes and shapes for the majority of applications. The strength of the metal fastener, however, is not achieved without costs. For many applications, metal can be relatively heavy, expensive, and subject to corrosion. Metal fasteners generally are not recyclable and, additionally, are neither biocompatilbe nor resorbable, when used in connection with medical applications.

Threaded, resorbable fasteners have existed in the prior art for medical applications, such as bone repair and regeneration. A typical resorbable fastener comprises a threaded shaft, a head, and an internal socket disposed within the head for accommodating a driver therein. This internal-socket fastener, although biocompatilbe and resorbable, has suffered from design deficiencies.

Since the prior art resorbable fastener is designed to be secured to bone within the human body, tissue or other debris may be introduced into the internal socket of the fastener. Materials introduced into the internal socket of the fastener can substantially attenuate or eliminate proper operability of the fastener. For example, a surgeon may have difficulty properly fitting a driver into the internal socket of a fastener that has become partially occluded with debris or human tissue. Since resorbable fasteners are generally manufactured having sizes on an order of millimeters, an obstruction of the very tiny internal socket of a fastener may be difficult to remove.

Although resorbable fasteners are inherently not as strong as metal fasteners with regard to rigidity, sheer strength, etc., resorbable fasteners offer very important benefits for medical applications, including biocompatability and resorbability. Since resorbable materials are relatively weak, as compared to the strength of metal, design considerations for resorbable fastener should maximize strength.

The specific internal-socket design of the prior art resorbable fastener does not appear to be particularly suited for medical and other applications where the strength of the non-magnetic fastener should be optimized. When a prior art internal-socket resorbable fastener is firmly secured into bone, for example, the driver may in some instances disrupt (strip) the internal socket of the fastener. Since the internal-socket is positioned along the rotational axis of the resorbable fastener, a very small moment arm must be utilized to rotate the fastener, resulting in the exertion by the driver of a relatively high rotational force onto the walls of the internal socket. The tiny construction of each internal-socket fastener (on the order of millimeters), the relatively weak material, and the relatively small application moment arm of the internal-socket fastener, all contribute to the relative sensitivity of the system. A need has thus existed in the prior art for a non-magnetic fastener having increased strength.

In additional to the limited strength associated with prior art non-magnetic fasteners, prior art non-magnetic fasteners have also suffered from relatively thick heads. As a result of the relatively weak material of the prior art internal-socket fastener, the head of the internal-socket fastener is typically manufactured to have a relatively thick dimension in a direction parallel to the rotational axis of the fastener. The thicker head of the prior art fastener provides a greater surface area for frictional application of torque by the driver upon insertion of the driver into the internal socket of the fastener. The relatively thick head of the prior art fastener, however, can undesirably protrude from the surface within which it is mounted, thus creating an undesirable non-flush surface.

As a result of the relatively small dimensions of the resorbable fasteners in the context of, for example, bone repair and regeneration applications, the tiny resorbable fasteners are prone to being improperly placed into the target structure. The prior art driver does not firmly hold the fastener and, accordingly, may not accurately align the axis of the fastener with the axis of the driver. The fastener can thus be inadvertently cross threaded or otherwise improperly secured within the target structure. Additionally, as a result of the relatively loose fit between the prior art fastener and driver, the fastener may become dislodged from the target structure and/or the driver, before being completely secured within the target structure.

Prior art drivers used to secure fasteners into target structures are typically not disposable. Accordingly, a single driver is used to secure a plurality of fasteners into the target structure or structures. The user is thus required to manually pick up and align each fastener with both the target structure and the driver, before the fastener can be secured within the target structure or structures. Additionally, due in part to the relatively tiny dimensions of the fastener, a user may accidentally obtain a fastener, having a size other than the desired size, and attempt to secure the improperly-sized fastener into the target structure. The process of manipulating the fastener from the operating table into the target structure, accordingly, can be time consuming and subject to human error. In medical applications, the handling of the fastener by the hand of the user and, further, the multiple uses of the driver on a plurality of fasteners, can increase a probability of infection.

SUMMARY OF THE INVENTION

The high-torque fastener of the present invention includes a threaded shaft and a star-shaped head. In a preferred embodiment, the high-torque fastener comprises a resorbable or other non-magnetic material. A mating driver snugly fits around the star-shaped head of the fastener, to thereby apply torque to the perimeter of the star-shaped head. Since the high-torque fastener does not incorporate an internal socket, the high-torque fastener of the present invention is immune from the prior art problem of the interior socket becoming obstructed with tissue or other debris.

In contrast to the prior art internal socket fastener, the high-torque fastener of the present invention harnesses a relatively large moment arm. Sufficient torque is generated, via frictional contact between the driver the perimeter of the star-shaped head, without the introduction of excessive and potentially destructive frictional forces being introduced onto the star-shaped head. In other words, since the high-torque fastener of the present invention utilizes a relatively large moment arm, a relatively small rotational force can be used to apply relatively high torque to the fastener of the present invention.

The star-shaped head of the high-torque fastener provides a relatively large surface contact area for application of frictional rotational forces by the driver and, further, facilitates a uniform distribution of torque about the perimeter of high-torque fastener of the present invention. The star-shaped head and the mating driver provide a system for applying relatively high rotational forces to the fastener to thereby firmly secure the fastener into a target structure. When removal of a resorbable, high-torque fastener is required, for example, the head of the high-torque fastener is not as susceptible to damage, compared to internal socket fasteners. The resulting high-torque fastener and driver combination of the present invention is more reliable and less subject to damage, compared to prior art internal socket systems, even when fasteners having sizes on the order of millimeters are used.

In accordance with one embodiment of the present invention, both the head of the high-torque fastener and the driver comprise tapered surfaces for providing a better frictional contact between the star-shaped head and the driver, when the target structure comprises a counter sunk surface or when the high-torque fastener is counter sunk. The enhances frictional contact from the tapered surfaces can increase the application of torque to the star-shaped head by the driver, when the target structure comprises a counter sunk surface or when the high-torque fastener is counter sunk.

Although prior art internal socket fasteners required relatively thick heads for increasing the surface area between the internal socket and the driver, the high-torque fasteners of the present invention can be constructed having relatively thin heads. Since the head of the high-torque fastener of the present invention is less susceptible to damage by the driver, the head may be manufactured having smaller proportions. When the head and the driver are tapered, and the high-torque fastener is secured within a counter sunk hole of a target structure, for example, the profile of the fastener of the present invention is further reduced. Accordingly, the high-torque fastener of the present invention can be secured into a target structure in such a way as to make the high-torque fastener less palpable to a patient.

The high-torque fastener and driver combination of the present invention is constructed to facilitate fast and easy centering of the fastener on the driver. The surface of the head of the high-torque fastener of the present invention is slightly rounded, and the edge forming the opening of the driver has a slight taper corresponding in radius to that of the surface of the head of the high-torque fastener. This centering feature of the present invention can attenuate the occurrence of improper loading of the high-torque fastener within the driver.

In accordance with another aspect of the present invention, the high-torque fastener and the driver are configured to snugly fit together. When the high-torque fastener is secured within the driver, any shaking of the driver by the hand of a user cannot dislodge the high-torque fastener therefrom. When the high-torque fastener is secured within the driver, a user can grip only the high-torque fastener and rotate the high-torque fastener without touching the driver, so that the driver is completely below the high-torque fastener, without the high-torque fastener becoming dislodged from the driver. During the rotating action, the driver does not contact any object except for the high-torque fastener. In accordance with yet another aspect of the present invention, the high-torque fastener snaps into the driver to thereby provide a firm and secure fit. The strong hold of the driver on the high-torque fastener helps to ensure proper alignment of the rotational axes of the fastener and driver and, further, prevents the high-torque fastener from inadvertently being dislodged.

An automatic ejection mechanism is provided in accordance with yet another aspect of the present invention, for partially ejecting the high-torque fastener from the driver, as the high-torque fastener is secured within a target structure or structures, to thereby facilitate removal of the driver from around the high-torque fastener after the high-torque fastener is secured within the target structure or structures.

In accordance with still another aspect of the present invention, the driver is supplied with a high-torque fastener pre-secured therein, and is disposable. The tedious prior art process of selecting a properly-sized fastener, orienting the fastener, and subsequently assisting in the alignment of the fastener between the target structure and the driver as the driver is used to rotate the fastener, is reduced or eliminated. Time is saved, resulting in saved costs in the operating room, for example. Additionally, potential errors from the selection of the wrong-sized fastener, or an inappropriate alignment of the fastener relative to either of the target structure or the driver, can be reduced or eliminated. The disposable driver and fastener combination of the present invention offers added convenience and reliability. Moreover, since a user does not have to directly handle the fastener and since the disposable driver is only used once, any likelihood of infection can be attenuated. In accordance with yet another aspect of the present invention, the disposable driver and fastener combination is sold in a sterilized package.

The present invention, together with additional features and advantages thereof, may best be understood by reference to the following description taken in connection with the accompanying illustrative drawings.

BRIEF DESCRIPTION OF THE DRAWINGS

FIG. 1 is a perspective view of a driver and fastener combination in accordance with a first presently preferred embodiment;

FIG. 2 is a side elevation view of a fastener in accordance with the first presently preferred embodiment;

FIG. 3 is a side elevation view of a driver and fastener combination in accordance with the present invention;

FIG. 4 is a top planar view of a fastener in accordance with the first presently preferred embodiment;

FIG. 5 is a bottom planar view of a driver in accordance with the first presently preferred embodiment;

FIG. 10 is a top planar view of a fastener in accordance with a second presently preferred embodiment;

FIG. 11 is a bottom planar view of a driver in accordance with the second presently preferred embodiment;

FIG. 12 is a cross-sectional view of a driver in accordance with the second presently preferred embodiment;

FIG. 13 is a side-elavation view of a fastener in accordance with the second presently preferred embodiment;

FIG. 14 is a top planar view of a fastener in accordance with another embodiment of the presently preferred invention;

FIG. 15 is a cross-sectional view of a fastener and driver combination wherein the fastener is partially secured into a target structure, in accordance with a third presently preferred embodiment; and FIG. 16 is a cross-sectional view of a fastener and driver combination wherein the fastener is fully inserted into the target structure, in accordance with the third presently preferred embodiment.

FIGS. 17A–C are schematic illustrations of buttress-style threads in accordance with the present invention.

DETAILED DESCRIPTION OF THE PREFERRED EMBODIMENTS

Figure 6:
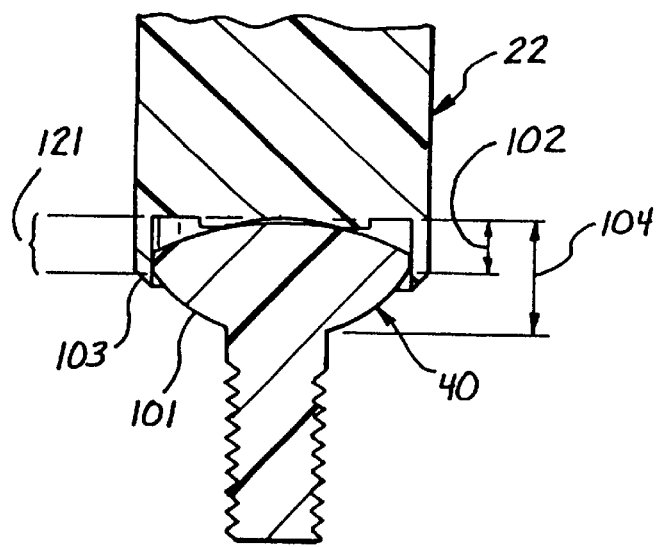
FIG. 6 is a cross-sectional view of a fastener and driver combination in accordance with the first presently preferred embodiment.

Referring now more particularly to the drawings, FIG. 1 illustrates a fastener and driver assembly 20 comprising a driver 22 and a high-torque fastener 24. The high-torque fastener 24 comprises a threaded shaft 26 having a shaft proximal end 28, a shaft distal end 31, and a shaft rotational axis 33 extending therebetween. A shaft diameter 36 (FIG. 2) is measured in a direction transverse to the shaft rotational axis 33.

The high-torque fastener 24 further comprises a head 40 which is connected to the shaft proximal end 28. As best seen in FIG. 2, the head 40 comprises a head proximal end 45, a head distal end 47, and a head rotational axis 49. A head diameter 51 is measured in a direction transverse to the head rotational axis 49, and a head perimeter 55 is defined as a surface of the head 40 surrounding a perimeter of the head 40.

The driver 22 comprises a driver opening 61 which is defined by an opening perimeter surface 63. As best seen in FIG. 3, the driver 22 comprises a driver proximal end 66, a driver distal end 68, and a driver rational axis 70 extending between the driver proximal end 66 and the driver distal end 68. The driver opening 61 is disposed within the driver 22 at the driver distal end 68 and is adapted for accommodating the head 40 of the high-torque fastener 24 therein.

As shown in FIGS. 1 and 2, the head proximal end 45 comprises a first curved surface 73 which has a substantially constant first radius of curvature and which is symmetrical about the head rotational axis 49. Referring particularly to FIG. 2, the first curved surface 73 can be expressed as follows. A first distance measured from a first point 81 on the first curved surface 73 near the head rotational axis 49 to a third point 84 on the shaft distal end 31, is greater than a second distance measured from a second point 86 near the head perimeter 55 on the first curved surface 73 to the third point 84 on the shaft distal end 31.

Figure 9:
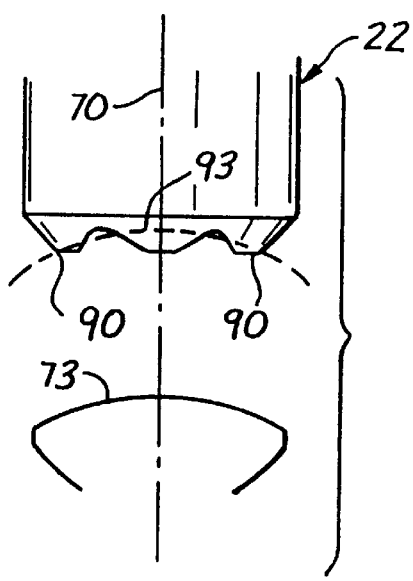
FIG. 9 is a side-elevation view of a fastener and driver combination in accordance with the first presently preferred embodiment.

Turning back to FIG. 1, the second curved surfaces 90 are disposed adjacent to the opening perimeter surface 63 to contact the first curved surface 73, when the head 40 is placed into contact with the second curved surfaces 90 in a rotationally misaligned manner. The phantom line 93 in FIG. 9 is drawn tangent to two of the second curved surfaces 90 and, further, is drawn to intersect the driver rotational axis 70. In the presently preferred embodiment, a radius of a curvature of the phantom line 93 is approximately equal to a radius of curvature of the first curved surface 73. A user placing the first curved surface 43 into contact with the second curved surfaces 90 of the opening perimeter surface 63, in a rotationally-misaligned orientation so that the head 40 does not fit into the driver opening 61, will experience a self-centering effect resulting from the first curved surface 73 of the head 40 and the second curved surfaces 90 of the opening perimeter 63. The self-centering effect tends to maintain an alignment of the shaft rotational axis 33 with the driver rotational axis 70, as the user rotates the high-torque fastener 24 about the shaft rotational axis 33 in an attempt to facilitate a proper fit of the head 40 within the driver opening 61. This self-centering feature of the present invention facilitates relatively easy loading of the high-torque fastener 24 into the driver 22.

Referring now to FIG. 4, the head 40 of the high-torque fastener 24 preferably comprises a plurality of radially-extending protrusions 96 spaced along the head perimeter 55. The radially-extending protrusions 96 are preferably evenly spaced along the head perimeter 55. The point of each radially extending protrusion 96 is preferably disposed a maximum radial distance away from the head rotational axis 49. The plurality of radially-extending protrusions 96 preferably form a star shape having six slightly-rounded points 96.

FIG. 5 is a bottom planar view of the driver 22, illustrating how the opening perimeter surface 63 very closely corresponds to the head perimeter 55 (FIG. 4), to thereby insure a snug fit between the two.

Although six radially-extending protrusions 96 are presently preferred, other numbers of points may be used in other modified embodiments. In the presently preferred embodiment, wherein relatively weak materials are used for the high-torque fastener 24, as compared to metal, and wherein the high-torque fastener 24 is manufactured to have a relatively small size of the order of millimeters, a maximum of six to eight points on the head 40 is preferred for maximum surface area, strength, and operability. In other embodiments, as few as 3 points and as many as 12 points may be used. In still other modified embodiments, fewer or substantially greater (20 or more) numbers of points may be used.

FIG. 10 illustrates a top planar view of a high-torque fastener 124 in accordance with a second preferred embodiment of the present invention, and FIG. 14 illustrates a top planar view of a high-torque fastener 224 in accordance with another modified embodiment of the present invention comprising only four points. Regardless of the particular configuration of the head of the high-torque fastener, the driver of the present invention is preferably precisely manufactured to snugly fit around the head perimeter of the high-torque fastener. In other non-interchangeable embodiments in connection with the use of other materials, for example, other numbers of points on the star-shaped head and other complimentary star-shaped driver openings may be used. Additionally, in other modified embodiments, the star shape may be changed to provide other shapes, such as a fluted, corrugated, or ribbed configurations. The star shape of the present invention provides for a greater surface area and, consequently, a better friction grip and larger distribution of the applied torque forces between the head of the high-torque fastener 24 and the opening perimeter surface 63 of the driver 22, as compared to the surface area of a conventional hex-head bolt, for example.

In accordance with the present invention, rotational forces are frictionally applied by the driver 22 to the head perimeter 55, to thereby distribute rotational forces around the head 40 of the high-torque fastener 24. As a result of the large moment arm, the strength of the high-torque fastener 24 is limited only by the inherent sheet strength of its material.

In a presently preferred embodiment, high-torque fasteners 24 are used to secure plates to bone for skeletal repair. High-torque fasteners 24 can also be used to secure sheets, meshes, and other membrane barriers, for example, to bone for skeletal repair. Co-pending U.S. application Ser. No. 08/699,673, filed on Aug. 19, 1996 and commonly assigned, discloses such membranes.

The high-torque fasteners 24, when used for skeletal repair or other surgical applications, are preferably relatively small in size. As presently embodied, the high-torque fasteners 24 are formed with shaft diameters 36 of 2 mm or 2.5 mm, and corresponding head diameters 51 of 3.7 mm. In another preferred embodiment, the high-torque fasteners 24 are formed having shaft diameters 36 of approximately 1.5 mm and head diameters 51 of approximately 2.8 mm. In modified embodiments, the high-torque fasteners 24 are formed with shaft diameters 36 from about 1 mm to about 5 mm.

The high-torque fasteners 24 preferably comprise non-magnetic materials. In skeletal repair applications, for example, the high-torque fasteners 24 preferably comprise resorbable materials and, to date, preferably comprise polymers and/or co-polymers made from lactic acid and/or glycolic acid. Other materials such as other resorbable or non-resorbable materials, including biocompatible materials, may also be used. The head diameters and other dimensions, including thread size, head design, shaft diameter, etc., may be made smaller, larger, or otherwise modified or changed depending on the particular application in accordance with other modified embodiments of the present invention. In addition to the above-mentioned shaft and head diameters, the relative dimensions depicted in FIGS. 1–16 are specifically contemplated by the present inventors.

FIG. 6 illustrates a cross-sectional view of the high-torque fastener 24 firmly secured within the driver 22. The first curved surface 73 is inserted into the driver opening 61 until the first curved surface 73 contacts an interior surface of the driver 22. In accordance with one embodiment, the contacting of the first curved surface 73 with an interior surface of the driver 22 results in a snap fit.

The snap fit is achieved, for example, when relatively large insertion forces are applied to move the high-torque fastener 24 into the driver 22. The relatively large insertion forces are initially met with frictional counter forces, resulting in a relatively slow movement of the high-torque fastener 24 into the driver 22 as insertion forces are maintained. The relatively large insertion forces, at an intermediate point in the insertion process, are met with somewhat reduced frictional forces, resulting in an acceleration of the high-torque fastener 24. The high-torque fastener 24 then travels a small distance until the first curved surface 73 contacts the interior surface of the driver 22 and then rapidly decelerates. The contacting of the first curved surface 73 with the interior surface of the driver 22 results in the snap fit, which provides a verification to the user that the high-torque fastener has been fully and properly seated with the driver 22. The verification of the snap fit can comprise an audible snap sound indicating that the high-torque fastener cannot be inserted further into the driver 22.

When the high-torque fastener 24 is firmly secured within the driver 22, the head perimeter 55 of the high-torque fastener 24 is frictionally engaged with the opening perimeter surface 63. The tapered portion 103 of the driver 22 tapers in a distal direction, from an area between the driver proximal end 66 and the driver distal end 68, decreasing in diameter to the driver distal end 68. The tapered portion 101 of the head 40 tapers in a distal direction from the head perimeter 55 to the shaft proximal end 28. In the presently preferred embodiment, the tapered portion 101 of the high-torque fastener 24 has a slope which is approximately equal to the tapered portion 103 of the driver 22. In a preferred embodiment, the slope forms an angle of 45 degrees with the shaft rotational axis 33 of the high-torque fastener 24.

Figure 7:
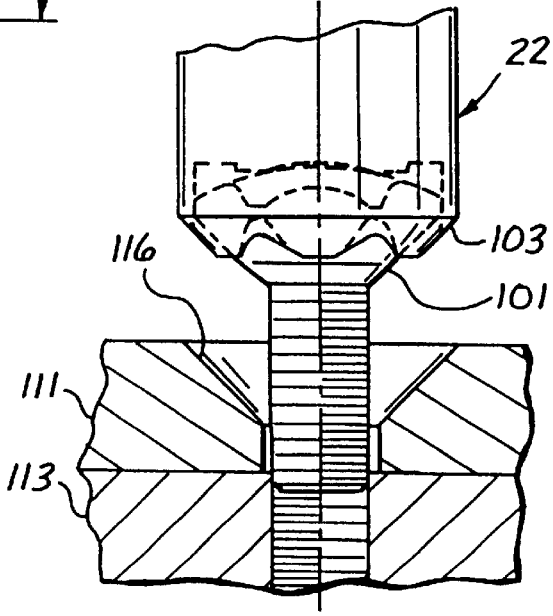
FIG. 7 is a side-elevation view of a fastener and driver combination wherein the fastener is partially inserted into two members, in accordance with the first presently preferred embodiment.
Figure 8:
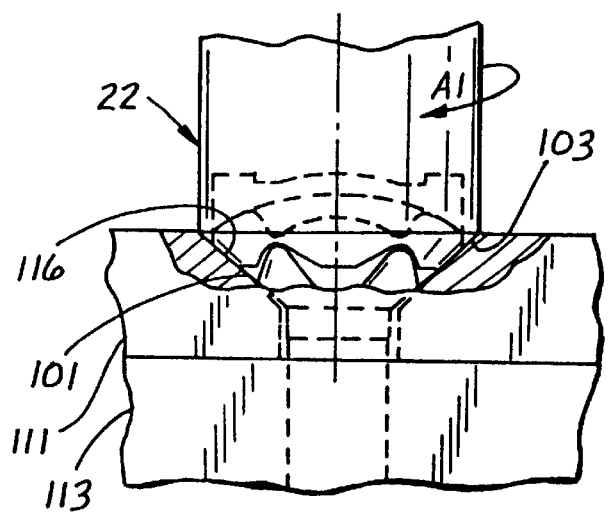
FIG. 8 is a cross-sectional view of a fastener and driver combination wherein the fastener is fully inserted into the two members, in accordance with the first presently preferred embodiment.

FIG. 7 shows that the tapered portion 101 of the head 40 is not flush with the tapered portion 103 of the driver 22 when the high-torque fastener 24 is fully secured within the driver 22. FIG. 8 shows how the tapered portion 103 of the driver 22 is substantially flush with the tapered portion 101 of the head 40 when the high-torque fastener 24 is completely secured into a target structure or structures. Rotation of the driver 22 in the direction of the arrow A1 threads the high-torque fastener 24 through a first object 111 and into a second object 113, such as bone. As shown in FIG. 7, a countersunk aperture 116 is preferably formed within each aperture of the first object 111.

The high-torque fastener 24 can be firmly secured within the first object 111 and the second object 113 by a user rotating the driver 22 in the direction of the arrow A1, as illustrated in FIG. 8. As the high-torque fastener 24 is fully secured into the first object 111 and the second object 113, the high-torque fastener 24 is partially self-extracted out of the driver opening 61 of the driver 22. FIG. 8 shows how the self-extraction partially removes the first curved surface 73 from contact with a portion of the driver 22. A relatively large amount of force is required to remove the driver 22 from the head 40, when the high-torque fastener 24 is fully seated within the driver 22, as illustrated in FIGS. 6 and 7, for example. After the high-torque fastener 24 is partially self-extracted as shown in FIG. 8, however, the driver 22 can be removed from around the head perimeter 55 of the high-torque fastener 24, with substantially less effort.

In accordance with a preferred embodiment of the present invention, the radius of curvature of the first curved surface 73 provides a varying thickness across the diameter of the head 40 while still reducing a palpability of the high-torque fastener 24 to a patient. Thicknesses of the head 40 vary with distance from the head rotational axis 33, so that portions of the head 40 closer to the head rotational axis 33 are thicker than portions further from the head rotational axis 33. Portions of the head 40 between the radially extending protrusions 196 are thicker than portions on the radially extending protrusions 196, as a result of the varying thickness across the diameter of the head 40. The thicker portions of the head 40 between the radially extending protrusions 196 help to provide a firm grip of the driver 22 about the high-torque fastener 24, especially when the high-torque fastener 24 is fully seated or almost fully seated. When the high-torque fastener 24 is fully seated or almost fully seated within, for example, the first object 111 and the second object 113, and is being either secured or removed, the thicker inner portions of the head 40 between the radially extending protrusions 196 enhance the strength of the head 40 and enhance the grip of the driver 22 about the head 40.

After the high-torque fastener 24 is fully secured into the first object 111 and second object 113, the driver 22 can be removed The driver 22 can subsequently be placed back around the head perimeter 55 of the high-torque fastener 24, to thereby facilitate removal of the high-torque fastener 24. After placing the opening perimeter surface 63 of the driver 22 over the head perimeter 55 of the high-torque fastener 24, a user can rotate the driver 22 in a direction opposite to the arrow A1, to thereby rotate the high-torque fastener 24 out of the first object 111 and the second object 113.

Rotation of the high-torque fastener 24 in a direction opposite to the arrow A1 results in movement of the high-torque fastener 24 in a direction toward the driver 22. After the high-torque fastener 24 has moved a predetermined distance in a direction from the first object 111 and the second object 113 toward the driver 22, the driver 22 can be pushed distally toward the first object 111 and the second object 113, to thereby fully and firmly seat the head 40 of the high-torque fastener 24 within the driver opening 61. When the head 40 is fully seated within the driver opening 61, the first curved surface 73 of the high-torque fastener 24 contacts an inner portion of the driver 22. This contacting results in a snap fit in accordance with one embodiment of the present invention. Accordingly, when the high-torque fastener 24 is inserted into the countersunk aperture 116, the countersunk aperture 116 forces the driver 22 off of the high-torque fastener 24 to some extent so that the driver 22 can be removed from the head 40 with relative ease when the high-torque fastener 24 is fully secured within the first object 111 and the second object 113.

The tapered portion 103 of the driver 22 is substantially flush with the tapered portion 101 of the high-torque fastener 24, when the high-torque fastener 24 is firmly secured within the first object 111 and the second object 113. The countersunk aperture 116 as presently embodied helps to flush mount the head 40 of the high-torque fastener 24 to the first object 111. The tapered portion 103 of the driver 22 is adapted to fit within the countersunk aperture 116 to thereby allow the opening perimeter surface 63 of the driver 22 to reach a maximum distance within the countersunk aperture 116 and fit around the head perimeter 55. Again, as the high-torque fastener 24 is removed from the first object 111 and the second object 113, the driver 22 can be pushed further onto the head 40 of the high-torque fastener 24, to thereby fully seat the high-torque fastener 24 within the driver 22.

In accordance with the present invention, a removal force required to remove the driver 22 from the head 40 in the fully seated position is greater than a removal force required to remove the driver 22 from the head 40 in the self-extracted position. As presently preferred, the removal force required to remove the driver 22 from the head 40 in the fully seated position is at least 10 percent and, more preferably at least 20 percent, greater than the removal force required to remove the driver 22 from the the head 40 in the self-extracted position. Even more preferably, the removable force for the fully seated position is twice and, more preferably ten times, as large as the removable force for the self-extracted position. Greater removal forces may be configured in modified embodiments. When the tapered portion 103 of the high-torque fastener 24 is fully within the countersunk aperture 116, a proximal portion 121 (FIG. 6) extends above the surface of the countersunk aperture 116, to facilitate gripping thereof by the opening perimeter surface 63 of the driver 22.

FIGS. 10–13 illustrate a second presently preferred embodiment of a high-torque fastener and driver combination, wherein like numbers are designated with like numerals preceded by a "1." The head 140 of the high-torque fastener 124 comprises a plurality of radially extending protrusions 196. A threaded shaft 126 is connected to the head 140. FIGS. 11 and 12 illustrate bottom planar and cross-sectional views of the driver 122, which comprises a driver distal end 168 having an opening perimeter surface 163 therein. The high-torque fastener 124 comprises a tapered portion 1101, as illustrated in FIG. 13.

Operation of the driver 122 and the high-torque fastener 124 is very similar to that of the high-torque fastener 24 and driver 22 discussed above. In a presently preferred embodiment, the driver 122 is constructed in a form similar to the driver 22, having a tapered portion parallel to the tapered portion 1101 of the high-torque fastener 124. In an embodiment where the driver 122 comprises a tapered portion, the high-torque fastener 124 is adapted to be secured into a countersunk hole so that the top surface of the high-torque fastener 124 is flush with a surface of the first object. In other embodiments, the high-torque fastener 124 comprises a first curved surface similar to the first curved surface 73 of the high-torque fastener 24, and the driver 122 comprise second curved surfaces similar to the second curved surfaces 90 of the driver 22.

FIG. 14 illustrates an embodiment of a high-torque fastener 224, wherein only four radially extending protrusions 296 are disposed about the head 240. FIGS. 15 and 16 illustrate a third preferred embodiment of the present invention, wherein like elements are designated with like numerals preceded by a "3". The driver 322 comprises tapered portions 3103 for contacting surfaces of a countersunk aperture 3116 of a first object 3111. In FIG. 15, a first curved surface 373 of the high-torque fastener 324 abuts against an inner surface of the driver 322. A head perimeter 355 contacts an opening perimeter surface 363 of the driver 322. The star or corrugated shape of the head 340 of the high-torque fastener 324 increases the surface of the driven area of the high-torque fastener 324 and allows the torque to be distributed and applied uniformly to the high-torque fastener 324. This structure when used in a countersunk aperture 3116 allows for a shallower head 340, relative to the prior art, which is critical to certain applications, such as, the use in surgery wherein the total thickness is important since the high-torque fastener 324 should not be palpable to the patient. FIG. 16 shows the high-torque fastener 324 in a self-extracted position, relative to the driver 322, wherein the first curved surface 373 of the high-torque fastener 324 is substantially flush with the surface of the first object 3111.

Since the depth of the driver opening 361 is greater than a height of the head 340, the driver 322 can be seated on the first object 3111 before the high-torque fastener 324 is fully seated, as shown in FIG. 15. By continuing to tighten the high-torque fastener 324, the high-torque fastener 324 is pulled from the driver 322, as shown in FIG. 16. The driver 322 may subsequently be removed from the head 340 with relative ease.

The tapered portion 3103 of the driver 322 is adapted to fit within the countersunk aperture 3116, even when the high-torque fastener 324 is fully seated therein, as shown in FIG. 16. If removal of the high-torque fastener 324 from the first object 3111 is required, there is more surface area on head 340 for the driver 322 to contact due to the countersunk-oriented structure. The removal of the high-torque fastener 324 is thus possible and easier, relative to the prior art, with less chance for damage to the head 340 of the high-torque fastener 324. Upon rotation of the driver 322 in a counterclockwise direction, the high-torque fastener 324 can be slightly removed from the countersunk aperture 3111, as illustrated in FIG. 15. As further shown in FIG. 15, after the high-torque fastener 324 is slightly removed from the countersunk aperture 311, the driver 322 can be pushed further over the high-torque fastener 324 to thereby firmly grip and fully seat the high-torque fastener 324 therein, thus facilitating centering of a rotational axis of the high-torque fastener 324 with a rotational axis of the driver 322.

The present inventors have discovered a number of unique ratios with regard to the configuration of the inventive high-torque fasteners. In accordance with the present invention, the ratio of the inner head diameter to the maximum head diameter should preferably be about .9 or less and, more preferably, should be about .7 or less. In FIG. 4, a ratio of an inner head diameter 41 to a maximum head diameter of the head 40 is approximately .71. In FIG. 10, a ratio of an inner head diameter 141 to a maximum head diameter 142 of the head 140 is approximately .69. FIG. 14 illustrates a head 240, wherein a ratio of an inner head diameter 241 to a maximum head diameter 242 is approximately .61. In the configuration of FIG. 13, a ratio of an inner head diameter 140a to a maximum head diameter 140b of the head 140 is approximately .57.

In accordance with the present invention, a ratio of a minimum diameter of the opening perimeter surface 63 of the driver 22 to maximum diameter a of the opening perimeter surface 63 of the driver 22 is approximately .71, as can be seen from FIG. 5. A ratio of a minimum diameter 164 of the opening perimeter surface 163 of the driver 22 to a maximum diameter 166 of the opening perimeter surface 163 of the driver 22 is approximately .69, as can be seen from FIG. 11.

A ratio of the shaft diameter to the inner head diameter is about .9 and, more preferably, is about .7. For example, as shown in FIG. 2, a ratio of the shaft diameter 36 to the inner head diameter is about .6.

In accordance with another embodiment of the present invention, a ratio of a maximum head thickness to a maximum head diameter is about .4, and a ratio of a maximum head thickness to the shaft diameter is about .8. For example, in FIG. 13 a ratio of a maximum head thickness 143a to the maximum head diameter 140b is about .44. Similarly, in FIG. 13, a ratio of the maximum head thickness 143a to the shaft diameter 140a is about .77.

As shown in FIG. 6, a height 102 of a proximal non-tapered portion to a total height 104 of the head 40 is about .51. As can be seen from FIG. 13, a ratio of a minimum head thickness 142 to a maximum head thickness 143a is about 59 percent. Especially in the context of resorbable high-torque fasteners for medical use, it is preferred to have a relatively high fastener-head to shaft ratio for the benefit of facilitating greater application of torque onto the fastener. Such a ratio may also facilitate a smaller fastener head thickness, which can render the fastener less palpable to the patient. Smaller diameter shafts can yield greater probabilities of the shaft sheering.

Turning now to FIGS. 17A–17C, the threads of the present invention preferably comprise buttress-style threads which are uneven on opposing sides thereof. As one example, the spiral ribs which encircle the shaft of the high-torque fastener and which define the thread, comprise one side which is zero degrees relative to a perpendicular line and another side which is 45 degrees relative to a perpendicular line, as shown in FIG. 12A. The perpendicular line is measured relative to an axis of the high-torque fastener. In the presently preferred embodiment, the 45 degree angle side of the rib defining the thread is on the leading side of the high-torque fastener, which is opposite to the head side of the high-torque fastener. In the presently preferred embodiment, as shown in FIG. 12B, the spiral ribs which encircle the shaft of the high-torque fastener and which define the thread, comprise one side which is seven degrees relative to a perpendicular line and another side which is 45 degrees relative to a perpendicular line. In an embodiment as shown in FIG. 12C, the spiral ribs which encircle the shaft of the high-torque fastener and which define the thread, comprise one side which is five degrees relative to a perpendicular line and another side which is 45 degrees relative to a perpendicular line, as shown in FIG. 12A. The sharp leading angle allows for easier (low torque) insertion and the flatter following angle requires greater (high torque) removal forces. The buttress-style threads can be configured in various shapes and sizes in modified embodiments.

In a preferred embodiment the driver and high-torque fastener are packaged as a unit in which the high-torque fastener is fully seated within the driver. In surgery, for instance, this feature eliminates the need for the nurse or surgeon to load the high-torque fastener into the driver, saving operating-room time and costs and, further, increasing convenience and reliability. Due in part to the extremely small size of the resorbable fasteners in general, the systems can be difficult to assemble in practice. The pre-assembled unit using a disposable driver in accordance with the present invention eliminates this problem.

The driver is color coded to indicate the size of the high-torque fastener to which the driver is attached, in accordance with one embodiment of the present invention. For example, the driver comprises a blue color to indicate that the attached high-torque fastener has a shaft diameter of 2 mm, and the driver comprises a color of red to indicate that the attached high-torque fastener has a shaft diameter of 1.5 mm. The color coding of the driver, in combination with the pre-attachment of the appropriately-sized high-torque fastener, can attenuate or eliminate any error of using an unintended high-torque fastener size. The high-torque fasteners may be color coded to indicate high-torque fastener size in addition to, or as an alternative to, color coding of the driver. This color coding of the high-torque fasteners, however, may add an undesirable or potentially hazardous substance for the patient to the resorbable implant. The high-torque fasteners preferably are resorbable and, to date, preferably comprise polymers and/or co-polymers made from lactic acid and/or glycolic acid. Other materials, such as other resorbable or non-resorbable materials, including bio-compatible materials, may be used in other embodiments.

The high-torque fastener and driver system of the present invention has particular applicability in a context of (1) providing efficient means of removably attaching a high-torque fastener to a driver and (2) providing added strength and operability to non-magnetic high-torque fasteners and fastening means. In other embodiments of the invention, the high-torque fasteners can comprise other non-magnetic materials, such as plastic, wood, resin, recyclable substances, etc. The term non-magnetic is used herein to refer to materials low in steel and iron, and other materials that do not significantly interact with magnets. Although the prior art has used magnets to attach metallic (containing steel or iron) fasteners to drivers, magnets would not work for non-magnetic high-torque fasteners, including titanium, aluminum, brass and/or stainless-steel fasteners.

Although the high-torque fastener and driver system of the present invention has been described in the context of medical applications, the system of the present invention can be used in a wide variety of other applications. For example, high-torque fasteners made of wood may be used with furniture. Additionally, recyclable high-torque fasteners may be used for securing recyclable products together.

The structure of the present invention, which facilitates a very snug fit of a high-torque fastener head to a driver, can be used with metal (including iron and steel) high-torque fasteners for conventional applications, as well. For example, a user may desire to inset a metal high-torque fastener into a blind area, such as a deep recess, where the high-torque fastener needs to be gripped by the driver and securely held. The high-torque fastener may need to be securely held for a given distance under vibrational or other turbulent conditions, for example.

According to the presently preferred embodiment, in the context of metal high-torque fasteners, for example, the high-torque fastener head and the driver configuration are precisely manufactured to ensure a snug fit between the two. The snug fit allows for the driver to securely and frictionally hold the head of the high-torque fastener. When additional frictional holding of the high-torque fastener by the driver is required, the thickness of the head, measured along an axis of the high-torque fastener, can be increased to thereby increase the surface-contacting area between the driver and the head of the high-torque fastener.

Although an exemplary embodiment of the invention has been shown and described, many other changes, modifications and substitutions, in addition to those set forth in the above paragraphs, may be made by one having ordinary skill in the art without necessarily departing from the spirit and scope of this invention.

What is claimed is:

1. A non-magnetic fastening device, comprising:
    a threaded shaft having a shaft proximal end, a shaft distal end, and a shaft rotational axis extending therebetween, the threaded shaft having a shaft diameter measured in a direction transverse to the rotational axis;
    a plurality of buttress threads disposed on the threaded shaft; and
    a head connected to the proximal end of the threaded shaft, the head having a head proximal end, a head distal end, and a head rotational axis extending therebetween, the head having a head diameter measured in a direction transverse to the head rotational axis and a head perimeter, the head distal end comprising a tapered portion having a first slope, the tapered portion of the head distal end tapers in a distal direction, the tapered portion of the head distal end beginning near the head perimeter and decreasing in diameter to the shaft proximal end, the head perimeter of the fastener forming a star shape.

2. A fastener and driver assembly, comprising:
    (a) a driver having a driver proximal end, a driver distal end and a driver rotational axis extending therebetween, the driver comprising a driver opening at the driver distal end; and
    (b) a resorbable fastener including:
        (i) a threaded shaft having a shaft proximal end, a shaft distal end, and a shaft rotational axis extending therebetween; and
        (ii) a head connected to the shaft proximal end, the head having a head proximal side, a head distal side, a head rotational axis extending therebetween, and a head perimeter connecting the head proximal side to the head distal side;
    (c) wherein the head of the fastener is sized and configured to be firmly and frictionally secured within the driver opening, so that the fastener cannot be separated from the driver by any shaking movement of the driver by a hand of a user, the shaking movement being defined as a motion wherein the only contact to the fastener and driver assembly is the user's hand, which contacts only the driver and which remains on the driver throughout the motion.

3. The fastener and driver assembly as set forth in claim 2, wherein:
    the head perimeter of the fastener forms a star shape; and
    the driver opening forms a star-shaped opening which generally corresponds in size and configuration to the star shape formed by the head perimeter of the fastener.

4. A method of securing a biocompatible screw into a bone, the biocompatilbe screw comprising a threaded shaft and a head, the head having a proximal side, a distal side secured to the threaded shaft, and a perimeter connecting the proximal side to the distal side, the method comprising the following steps:
    securing the perimeter of the head to a driver, the driver surrounding and frictionally gripping the perimeter of the head but not contacting the distal side of the head, the head being frictionally secured to the driver along the perimeter so that the head cannot be separated from the driver by any shaking movement of the driver by a hand of a user, the shaking movement being defined as a motion wherein the only contact to the biocompatible screw and driver is the user's hand, which contacts only the driver and which remains on the driver throughout the motion; and
    rotating the driver to apply rotational forces onto the biocompatible screw, wherein the rotational forces are applied to the perimeter of the head of the biocompatible screw to thereby rotate the biocompatible screw and secure the screw into the bone.

5. The method of securing a biocompatible screw into a bone as set forth in claim 4, wherein the step of rotating the driver comprises a step of the driver applying torque to a star-shaped head perimeter of the head with a corresponding star-shaped opening in the driver.

6. A method of securing a screw into a countersunk hole of a bone plate and also into a bone, the screw comprising a threaded shaft and a tapered head portion shaped to fit snugly into the countersunk hole of the bone plate, the method comprising the following steps:

securing the perimeter of the head to a driver, the driver having a distal end, and the driver surrounding and frictionally gripping the perimeter of the head;

rotating the driver to apply torque onto the biocompatible screw, wherein the torque is applied to the perimeter of the head of the biocompatilbe screw to thereby rotate and advance the biocompatible screw into the countersunk hole; the driver being rotated and advanced, until the distal end of the driver contacts the countersunk hole but the tapered head portion of the biocompatible screw does not yet touch the countersunk hole;

continuing to rotate the driver while the distal end of the driver remains in contact with the countersunk hole and the distal end does not advance, the continued rotation of the driver further advancing the biocompatible screw until a time when the tapered head portion of the biocompatible screw contacts and snugly fits into the countersunk hole, whereby the biocompatible screw is at least partially ejected from the driver by the time the tapered head portion snugly fits into the countersunk hole.

7. The method of securing a biocompatible screw into a bone as set forth in claim 6, wherein the further advancing of the biocompatible screw while the distal end of the driver remains in contact with the countersunk hole advances the biocompatible screw and thus serves to at least partially eject the biocompatilbe screw from the driver.

8. The method of securing a biocompatible screw into a bone as set forth in claim 7, wherein the further advancing of the biocompatible screw and the at least partial ejection facilitates removal of the driver from around the biocompatible screw after the biocompatilbe screw has been tightened with a proper application of torque and secured within the bone plate and bone.

9. The method of securing a biocompatilbe screw into a bone as set forth in claim 8, wherein the biocompatilbe screw comprises a resorbable screw with a star-shaped head.

* * * * *